(12) United States Patent
Tabata et al.

(10) Patent No.: US 9,463,262 B2
(45) Date of Patent: Oct. 11, 2016

(54) CELL ADHESIVE MATERIAL FOR BIOLOGICAL TISSUE

(75) Inventors: Yasuhiko Tabata, Uji (JP); Shingo Kawabata, Kyoto (JP)

(73) Assignees: SANYO CHEMICAL INDUSTRIES, LTD., Kyoto-shi (JP); YASUHIKO TABATA, Uji-shi (JP)

( * ) Notice: Subject to any disclaimer, the term of this patent is extended or adjusted under 35 U.S.C. 154(b) by 190 days.

(21) Appl. No.: 13/882,857

(22) PCT Filed: Nov. 1, 2011

(86) PCT No.: PCT/JP2011/075139
§ 371 (c)(1),
(2), (4) Date: May 1, 2013

(87) PCT Pub. No.: WO2012/060351
PCT Pub. Date: May 10, 2012

(65) Prior Publication Data
US 2013/0289254 A1 Oct. 31, 2013

(30) Foreign Application Priority Data
Nov. 4, 2010 (JP) ................................ 2010-247740

(51) Int. Cl.
*A61K 39/00* (2006.01)
*A61K 39/02* (2006.01)
*A61K 39/04* (2006.01)
*A61L 27/22* (2006.01)
*A61L 27/38* (2006.01)
*A61L 27/54* (2006.01)

(52) U.S. Cl.
CPC .............. *A61L 27/22* (2013.01); *A61L 27/227* (2013.01); *A61L 27/3804* (2013.01); *A61L 27/54* (2013.01); *A61L 2300/25* (2013.01); *A61L 2300/252* (2013.01); *A61L 2420/02* (2013.01)

(58) Field of Classification Search
CPC ...................................................... A61F 13/02
USPC ................ 427/2.1, 2.31; 424/184.1; 428/423
See application file for complete search history.

(56) References Cited

U.S. PATENT DOCUMENTS

| 2002/0111694 A1 | 8/2002 | Ellingsen et al. |
| 2005/0079198 A1 | 4/2005 | Nies et al. |
| 2009/0018642 A1* | 1/2009 | Benco .......................... 623/1.15 |

FOREIGN PATENT DOCUMENTS

| EP | 1 512 773 A1 | 3/2005 |
| JP | 2004-515276 A | 5/2004 |
| JP | 2005-021208 A | 1/2005 |
| JP | 2005-058772 A | 3/2005 |
| JP | 2005-170810 A | 6/2005 |
| JP | 2007-051127 A | 3/2007 |
| JP | 2010-502363 A | 1/2010 |
| WO | 2006/004778 A2 | 1/2006 |
| WO | 2008/030388 A2 | 3/2008 |
| WO | 2008/127964 A2 | 10/2008 |
| WO | 2009/154961 A2 | 12/2009 |
| WO | WO2009/154961 * | 12/2009 ............. A61L 31/02 |

OTHER PUBLICATIONS

Xinyan, C., et al. "Placement of biomaterials and cells on University of Michigan neuroprobes". J. Disorders of the Newvous System and Aging, Society for Neuroscience Abstracts, 2000, vol. 26, No. 1-2, Abstract.*
Translation of the International Preliminary Report on Patentability (PCT/ISA/237) (5 pages), (PCT/IB/373) (1 page) of International Application No. PCT/JP2011/075139 mailed May 16, 2013 (Form PCT/IB/338) (1 page).
International Search Report for PCT/JP2011/075139, mailing date of Jan. 17, 2012.
Extended European Search Report dated Feb. 20, 2015, issued in corresponding application No. 11838001.3 (9 pages).
Xinyan C et al., "Placement of biomaterials and cells on University of Michigan neuroprobes", Database Biosis [Online] Biosciences Information Service, XP 002733957 (2 pages), 2000.
"Novel cell-adhesive peptide contained in base material, comprising cell adhesive artificial peptide and implant material, useful for implants such as artificial organs", Database WPI, Week 200409, Thomson Scientific, XP002733962 (4 pages), Jan. 8, 2004.
"Novel polypeptide having cell adhesion property, useful for culturing cells and producing bioactive substances", Database WPI Week 200553, Thomson Scientific, XP002733963 (4 pages), Jun. 30, 2005.
Toshinaga Maeda et al., "Cell Adhesion Signals: Focusing on Extracellular Matrix Adhesion Molecules and Their Receptor's Molecule Recognition Mechanisms", Journal of Osaka Medical Center and research institute of maternal and child heath, vol. 8, No. 1, pp. 58-66, 1992. With partial translation.

(Continued)

*Primary Examiner* — Rodney P Swartz
(74) *Attorney, Agent, or Firm* — Westerman, Hattori, Daniels & Adrian, LLP

(57) ABSTRACT

An object of the present invention is to provide a cell-adhesive material for biological tissues, in which the surface of a material for biological tissues (particularly metallic material) is modified strongly with a large amount of a cell-adhesive artificial peptide (P) that retains a biological activity.
The present invention provides a cell-adhesive material for biological tissues including a cell-adhesive artificial peptide (P) and a material for biological tissues, wherein the cell-adhesive artificial peptide (P) is immobilized on the surface of the material for biological tissues through an electrochemical reaction. The cell-adhesive artificial peptide (P) is preferably a peptide (P1) that is synthesized by a genetic recombinant microorganism and has at least one cell-adhesive minimal amino acid sequence (X) in one molecule. The number of the cell-adhesive minimal amino acid sequences (X) in one molecule of the polypeptide (P1) is preferably 3 to 50.

12 Claims, No Drawings

(56) References Cited

OTHER PUBLICATIONS

Toshinaga Maeda et al., "Artificial Cell Adhesive Proteins", Pathologic Physiology, vol. 9, No. 7, pp. 527-535, 1990. With partial translation.

Iwanami Koza, "Transplantation and artificial organs", Basis of modern medicine, vol. 14, published by Iwanami Shoten (1 page), 2001. With partial translation.

Dozin Co., Ltd., "Biochemical experiment course 1", Protein Chemistry IV (edited by the Japan Society of Biochemistry), published by Tokyo Kagaku Dozin Co., Ltd. (6 pages), Jul. 1, 1981. With partial translation.

Office Action dated Jul. 14, 2015, issued in counterpart Japanese Application No. 2012-541864 (w/ English translation) (8 pages).

English Translation of Japanese Patent No. 2005-170810, issued Jun. 30, 2005 (previously cited in May 1, 2013 Information Disclosure Statement) (18 pages).

* cited by examiner

```
SEQUENCE LISTING

<160> NUMBER OF SEQ ID NOS: 28

<210> SEQ ID NO 1
<211> LENGTH: 3
<212> TYPE: PRT
<213> ORGANISM: Artificial Sequence
<220> FEATURE:
<223> OTHER INFORMATION: Chemically Synthesized

<400> SEQUENCE: 1

Arg Gly Asp
1

<210> SEQ ID NO 2
<211> LENGTH: 3
```

```
<212> TYPE: PRT
<213> ORGANISM: Artificial Sequence
<220> FEATURE:
<223> OTHER INFORMATION: Chemically Synthesized

<400> SEQUENCE: 2

Leu Asp Val
1

<210> SEQ ID NO 3
<211> LENGTH: 4
<212> TYPE: PRT
<213> ORGANISM: Homo sapiens

<400> SEQUENCE: 3

Arg Glu Asp Val
1

<210> SEQ ID NO 4
<211> LENGTH: 5
<212> TYPE: PRT
<213> ORGANISM: Homo sapiens

<400> SEQUENCE: 4

Tyr Ile Gly Ser Arg
1               5

<210> SEQ ID NO 5
<211> LENGTH: 5
<212> TYPE: PRT
<213> ORGANISM: Homo sapiens

<400> SEQUENCE: 5

Pro Asp Ser Gly Arg
1               5

<210> SEQ ID NO 6
<211> LENGTH: 7
<212> TYPE: PRT
<213> ORGANISM: Homo sapiens

<400> SEQUENCE: 6

Arg Tyr Val Val Leu Pro Arg
1               5

<210> SEQ ID NO 7
<211> LENGTH: 6
<212> TYPE: PRT
<213> ORGANISM: Homo sapiens

<400> SEQUENCE: 7

Leu Gly Thr Ile Pro Gly
1               5

<210> SEQ ID NO 8
<211> LENGTH: 10
<212> TYPE: PRT
<213> ORGANISM: Homo sapiens

<400> SEQUENCE: 8

Arg Asn Ile Ala Glu Ile Ile Lys Asp Ile
1               5                   10

<210> SEQ ID NO 9
<211> LENGTH: 5
```

```
<212> TYPE: PRT
<213> ORGANISM: Homo sapiens

<400> SEQUENCE: 9

Ile Lys Val Ala Val
1               5

<210> SEQ ID NO 10
<211> LENGTH: 3
<212> TYPE: PRT
<213> ORGANISM: Homo sapiens

<400> SEQUENCE: 10

Leu Arg Glu
1

<210> SEQ ID NO 11
<211> LENGTH: 4
<212> TYPE: PRT
<213> ORGANISM: Homo sapiens

<400> SEQUENCE: 11

Asp Gly Glu Ala
1

<210> SEQ ID NO 12
<211> LENGTH: 3
<212> TYPE: PRT
<213> ORGANISM: Mytilus edulis

<400> SEQUENCE: 12

His Ala Val
1

<210> SEQ ID NO 13
<211> LENGTH: 15
<212> TYPE: PRT
<213> ORGANISM: Homo sapiens

<400> SEQUENCE: 13

Gly Val Lys Gly Asp Lys Gly Asn Pro Gly Trp Pro Gly Ala Pro
1               5                   10                  15

<210> SEQ ID NO 14
<211> LENGTH: 13
<212> TYPE: PRT
<213> ORGANISM: Homo sapiens

<400> SEQUENCE: 14

Gly Glu Phe Tyr Phe Asp Leu Arg Leu Lys Gly Asp Lys
1               5                   10

<210> SEQ ID NO 15
<211> LENGTH: 8
<212> TYPE: PRT
<213> ORGANISM: Homo sapiens

<400> SEQUENCE: 15

Tyr Lys Leu Asn Val Asn Asp Ser
1               5

<210> SEQ ID NO 16
<211> LENGTH: 10
<212> TYPE: PRT
<213> ORGANISM: Homo sapiens
```

```
<400> SEQUENCE: 16

Ala Lys Pro Ser Tyr Pro Pro Thr Tyr Lys
1               5                   10

<210> SEQ ID NO 17
<211> LENGTH: 12
<212> TYPE: PRT
<213> ORGANISM: Homo sapiens

<400> SEQUENCE: 17

Asn Arg Trp His Ser Ile Tyr Ile Thr Arg Phe Gly
1               5                   10

<210> SEQ ID NO 18
<211> LENGTH: 12
<212> TYPE: PRT
<213> ORGANISM: Homo sapiens

<400> SEQUENCE: 18

Thr Trp Tyr Lys Ile Ala Phe Gln Arg Asn Arg Lys
1               5                   10

<210> SEQ ID NO 19
<211> LENGTH: 12
<212> TYPE: PRT
<213> ORGANISM: Homo sapiens

<400> SEQUENCE: 19

Arg Lys Arg Leu Gln Val Gln Leu Ser Thr Arg Thr
1               5                   10

<210> SEQ ID NO 20
<211> LENGTH: 5
<212> TYPE: PRT
<213> ORGANISM: Homo sapiens

<400> SEQUENCE: 20

Pro His Ser Arg Asn
1               5

<210> SEQ ID NO 21
<211> LENGTH: 6
<212> TYPE: PRT
<213> ORGANISM: Artificial Sequence
<220> FEATURE:
<223> OTHER INFORMATION: auxiliary amino acid sequence

<400> SEQUENCE: 21

Gly Ala Gly Ala Gly Ser
1               5

<210> SEQ ID NO 22
<211> LENGTH: 54
<212> TYPE: PRT
<213> ORGANISM: Artificial Sequence
<220> FEATURE:
<223> OTHER INFORMATION: Chemically Synthesized

<400> SEQUENCE: 22

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30
```

Gly Ala Gly Ser Gly Ala Gly Ala Gly Ser Gly Ala Gly Ala Gly Ser
            35                  40                  45

Gly Ala Gly Ala Gly Ser
     50

<210> SEQ ID NO 23
<211> LENGTH: 980
<212> TYPE: PRT
<213> ORGANISM: Artificial Sequence
<220> FEATURE:
<223> OTHER INFORMATION: Obtained by Genetic Recombination

<400> SEQUENCE: 23

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
            35                  40                  45

Ser Gly Ala Gly Ala Gly Ser Gly Ala Gly Ala Gly Ser Gly Ala Gly
        50                  55                  60

Ala Gly Ser Gly Ala Gly Ala Gly Ser Gly Ala Ala Val Thr Gly Arg
65                  70                  75                  80

Gly Asp Ser Pro Ala Ser Ala Ala Gly Tyr Gly Ala Gly Ala Gly Ser
                85                  90                  95

Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
            115                 120                 125

Gly Ala Gly Ser Gly Ala Gly Ala Gly Ser Gly Ala Gly Ala Gly Ser
            130                 135                 140

Gly Ala Ala Val Thr Gly Arg Gly Asp Ser Pro Ala Ser Ala Ala Gly
145                 150                 155                 160

Tyr Gly Ala Gly Ala Gly Ser Gly Ala Gly Ala Gly Ser Gly Ala Gly
                165                 170                 175

Ala Gly Ser Gly Ala Gly Ala Gly Ser Gly Ala Gly Ala Gly Ser Gly
            180                 185                 190

Ala Gly Ala Gly Ser Gly Ala Gly Ala Gly Ser Gly Ala Gly Ala Gly
            195                 200                 205

Ser Gly Ala Gly Ala Gly Ser Gly Ala Ala Val Thr Gly Arg Gly Asp
        210                 215                 220

Ser Pro Ala Ser Ala Ala Gly Tyr Gly Ala Gly Ala Gly Ser Gly Ala
225                 230                 235                 240

Gly Ala Gly Ser Gly Ala Gly Ala Gly Ser Gly Ala Gly Ala Gly Ser
                245                 250                 255

Gly Ala Gly Ala Gly Ser Gly Ala Gly Ala Gly Ser Gly Ala Gly Ala
            260                 265                 270

Gly Ser Gly Ala Gly Ala Gly Ser Gly Ala Gly Ala Gly Ser Gly Ala
            275                 280                 285

Ala Val Thr Gly Arg Gly Asp Ser Pro Ala Ser Ala Ala Gly Tyr Gly
            290                 295                 300

Ala Gly Ala Gly Ser Gly Ala Gly Ala Gly Ser Gly Ala Gly Ala Gly
305                 310                 315                 320

Ser Gly Ala Gly Ala Gly Ser Gly Ala Gly Ala Gly Ser Gly Ala Gly
                325                 330                 335

```
Ala Gly Ser Gly Ala Gly Ala Gly Ser Gly Ala Gly Ser Gly
            340                 345                 350

Ala Gly Ala Gly Ser Gly Ala Ala Val Thr Gly Arg Gly Asp Ser Pro
            355                 360                 365

Ala Ser Ala Ala Gly Tyr Gly Ala Gly Ala Gly Ser Gly Ala Gly Ala
        370                 375                 380

Gly Ser Gly Ala Gly Ala Gly Ser Gly Ala Gly Ala Gly Ser Gly Ala
385                 390                 395                 400

Gly Ala Gly Ser Gly Ala Gly Ala Gly Ser Gly Ala Gly Ala Gly Ser
                405                 410                 415

Gly Ala Gly Ala Gly Ser Gly Ala Gly Ala Gly Ser Gly Ala Ala Val
                420                 425                 430

Thr Gly Arg Gly Asp Ser Pro Ala Ser Ala Ala Gly Tyr Gly Ala Gly
            435                 440                 445

Ala Gly Ser Gly Ala Gly Ala Gly Ser Gly Ala Gly Ala Gly Ser Gly
            450                 455                 460

Ala Gly Ala Gly Ser Gly Ala Gly Ala Gly Ser Gly Ala Gly Ala Gly
465                 470                 475                 480

Ser Gly Ala Gly Ala Gly Ser Gly Ala Gly Ala Gly Ser Gly Ala Gly
                485                 490                 495

Ala Gly Ser Gly Ala Ala Val Thr Gly Arg Gly Asp Ser Pro Ala Ser
            500                 505                 510

Ala Ala Gly Tyr Gly Ala Gly Ala Gly Ser Gly Ala Gly Ala Gly Ser
            515                 520                 525

Gly Ala Gly Ala Gly Ser Gly Ala Gly Ala Gly Ser Gly Ala Gly Ala
530                 535                 540

Gly Ser Gly Ala Gly Ala Gly Ser Gly Ala Gly Ala Gly Ser Gly Ala
545                 550                 555                 560

Gly Ala Gly Ser Gly Ala Gly Ala Gly Ser Gly Ala Ala Val Thr Gly
                565                 570                 575

Arg Gly Asp Ser Pro Ala Ser Ala Ala Gly Tyr Gly Ala Gly Ala Gly
            580                 585                 590

Ser Gly Ala Gly Ala Gly Ser Gly Ala Gly Ala Gly Ser Gly Ala Gly
            595                 600                 605

Ala Gly Ser Gly Ala Gly Ala Gly Ser Gly Ala Gly Ala Gly Ser Gly
            610                 615                 620

Ala Gly Ala Gly Ser Gly Ala Gly Ala Gly Ser Gly Ala Gly Ala Gly
625                 630                 635                 640

Ser Gly Ala Ala Val Thr Gly Arg Gly Asp Ser Pro Ala Ser Ala Ala
                645                 650                 655

Gly Tyr Gly Ala Gly Ala Gly Ser Gly Ala Gly Ala Gly Ser Gly Ala
            660                 665                 670

Gly Ala Gly Ser Gly Ala Gly Ala Gly Ser Gly Ala Gly Ala Gly Ser
            675                 680                 685

Gly Ala Gly Ala Gly Ser Gly Ala Gly Ala Gly Ser Gly Ala Gly Ala
            690                 695                 700

Gly Ser Gly Ala Gly Ala Gly Ser Gly Ala Ala Val Thr Gly Arg Gly
705                 710                 715                 720

Asp Ser Pro Ala Ser Ala Ala Gly Tyr Gly Ala Gly Ala Gly Ser Gly
                725                 730                 735

Ala Gly Ala Gly Ser Gly Ala Gly Ala Gly Ser Gly Ala Gly Ala Gly
            740                 745                 750

Ser Gly Ala Gly Ala Gly Ser Gly Ala Gly Ala Gly Ser Gly Ala Gly
```

```
                755                 760                 765
Ala Gly Ser Gly Ala Gly Ala Gly Ser Gly Ala Gly Ala Gly Ser Gly
        770                 775                 780
Ala Ala Val Thr Gly Arg Gly Asp Ser Pro Ala Ser Ala Ala Gly Tyr
785                 790                 795                 800
Gly Ala Gly Ala Gly Ser Gly Ala Gly Ala Gly Ser Gly Ala Gly Ala
                    805                 810                 815
Gly Ser Gly Ala Gly Ala Gly Ser Gly Ala Gly Ala Gly Ser Gly Ala
            820                 825                 830
Gly Ala Gly Ser Gly Ala Gly Ala Gly Ser Gly Ala Gly Ala Gly Ser
        835                 840                 845
Gly Ala Gly Ala Gly Ser Gly Ala Ala Val Thr Gly Arg Gly Asp Ser
    850                 855                 860
Pro Ala Ser Ala Ala Gly Tyr Gly Ala Gly Ala Gly Ser Gly Ala Gly
865                 870                 875                 880
Ala Gly Ser Gly Ala Gly Ala Gly Ser Gly Ala Gly Ala Gly Ser Gly
                    885                 890                 895
Ala Gly Ala Gly Ser Gly Ala Gly Ala Gly Ser Gly Ala Gly Ala Gly
            900                 905                 910
Ser Gly Ala Gly Ala Gly Ser Gly Ala Gly Ala Gly Ser Gly Ala Ala
        915                 920                 925
Val Thr Gly Arg Gly Asp Ser Pro Ala Ser Ala Ala Gly Tyr Gly Ala
    930                 935                 940
Gly Ala Gly Ser Gly Ala Gly Ala Gly Ser Gly Ala Gly Ala Met Asp
945                 950                 955                 960
Pro Gly Arg Tyr Gln Leu Ser Ala Gly Arg Tyr His Tyr Gln Leu Val
                965                 970                 975
Trp Cys Gln Lys
            980

<210> SEQ ID NO 24
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 24

Gly Ala Gly Ala Gly Ser Gly Ala Gly Ala Gly Ser Gly Ala Gly Ala
1               5                   10                  15

Gly Ser

<210> SEQ ID NO 25
<211> LENGTH: 251
<212> TYPE: PRT
<213> ORGANISM: Artificial Sequence
<220> FEATURE:
<223> OTHER INFORMATION: Obtained by Genetic Recombination

<400> SEQUENCE: 25

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Ala Val Thr Gly Arg Gly Asp
```

```
                          50                  55                  60
Ser Pro Ala Ser Ala Ala Gly Tyr Gly Ala Gly Ala Gly Ser Gly Ala
 65                  70                  75                  80

Gly Ala Gly Ser Gly Ala Gly Ala Gly Ser Gly Ala Ala Val Thr Gly
                 85                  90                  95

Arg Gly Asp Ser Pro Ala Ser Ala Ala Gly Tyr Gly Ala Gly Ala Gly
                100                 105                 110

Ser Gly Ala Gly Ala Gly Ser Gly Ala Gly Ala Gly Ser Gly Gly Ala
                115                 120                 125

Ala Val Thr Gly Arg Gly Asp Ser Pro Ala Ser Ala Ala Gly Tyr Gly
        130                 135                 140

Ala Gly Ala Gly Ser Gly Ala Gly Ala Gly Ser Gly Ala Gly Ala Gly
145                 150                 155                 160

Ser Gly Ala Ala Val Thr Gly Arg Gly Asp Ser Pro Ala Ser Ala Ala
                165                 170                 175

Gly Tyr Gly Ala Gly Ala Gly Ser Gly Ala Gly Ala Gly Ser Gly Ala
            180                 185                 190

Gly Ala Gly Ser Gly Ala Ala Val Thr Gly Arg Gly Asp Ser Pro Ala
        195                 200                 205

Ser Ala Ala Gly Tyr Gly Ala Gly Ala Gly Ser Gly Ala Gly Ala Gly
            210                 215                 220

Ser Gly Ala Gly Ala Met Asp Pro Gly Arg Tyr Gln Leu Ser Ala Gly
225                 230                 235                 240

Arg Tyr His Tyr Gln Leu Val Trp Cys Gln Lys
                245                 250

<210> SEQ ID NO 26
<211> LENGTH: 181
<212> TYPE: PRT
<213> ORGANISM: Artificial Sequence
<220> FEATURE:
<223> OTHER INFORMATION: Obtained by Genetic Recombination

<400> SEQUENCE: 26

Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Ala Gly Ala Gly
            35                  40                  45

Ser Gly Ala Gly Ala Gly Ser Gly Ala Ala Val Thr Gly Arg Gly Asp
        50                  55                  60

Ser Pro Ala Ser Ala Ala Gly Tyr Gly Ala Gly Ala Gly Ser Gly Ala
 65                  70                  75                  80

Gly Ala Gly Ser Gly Ala Gly Ala Gly Ser Gly Ala Ala Val Thr Gly
                 85                  90                  95

Arg Gly Asp Ser Pro Ala Ser Ala Ala Gly Tyr Gly Ala Gly Ala Gly
                100                 105                 110

Ser Gly Ala Gly Ala Gly Ser Gly Ala Gly Ala Gly Ser Gly Gly Ala
                115                 120                 125

Ala Val Thr Gly Arg Gly Asp Ser Pro Ala Ser Ala Ala Gly Tyr Gly
        130                 135                 140

Ala Gly Ala Gly Ser Gly Ala Gly Ala Gly Ser Gly Ala Gly Ala Met
145                 150                 155                 160

Asp Pro Gly Arg Tyr Gln Leu Ser Ala Gly Arg Tyr His Tyr Gln Leu
```

```
                        165                 170                 175

Val Trp Cys Gln Lys
            180

<210> SEQ ID NO 27
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 27

Arg Lys Leu Pro Asp Ala
1               5

<210> SEQ ID NO 28
<211> LENGTH: 861
<212> TYPE: PRT
<213> ORGANISM: Artificial Sequence
<220> FEATURE:
<223> OTHER INFORMATION: Obtained by Genetic Recombination

<400> SEQUENCE: 28

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Ala Val Thr Gly Arg Gly Asp Ser Pro
        35                  40                  45

Ala Ser Ala Ala Gly Tyr Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ser Gly Ala Gly Ala Gly Ser
                85                  90                  95

Gly Ala Gly Ala Gly Ser Gly Ala Gly Ala Gly Ser Arg Lys Leu Pro
            100                 105                 110

Asp Ala Gly Ala Gly Ala Gly Ser Gly Ala Gly Ala Gly Ser Gly Ala
        115                 120                 125

Gly Ala Gly Ser Gly Ala Gly Ala Gly Ser Gly Ala Gly Ala Gly Ser
    130                 135                 140

Gly Ala Gly Ala Gly Ser Gly Ala Gly Ala Gly Ser Gly Ala Gly Ala
145                 150                 155                 160

Gly Ser Gly Ala Gly Ala Gly Ser Ala Ala Val Thr Gly Arg Gly
                165                 170                 175

Asp Ser Pro Ala Ser Ala Ala Gly Tyr Gly Ala Gly Ala Gly Ser Gly
            180                 185                 190

Ala Gly Ala Gly Ser Gly Ala Gly Ala Gly Ser Gly Ala Gly Ala Gly
        195                 200                 205

Ser Gly Ala Gly Ala Gly Ser Gly Ala Gly Ala Gly Ser Gly Ala Gly
    210                 215                 220

Ala Gly Ser Gly Ala Gly Ala Gly Ser Gly Ala Gly Ala Gly Ser Arg
225                 230                 235                 240

Lys Leu Pro Asp Ala Gly Ala Gly Ala Gly Ser Gly Ala Gly Ala Gly
                245                 250                 255

Ser Gly Ala Gly Ala Gly Ser Gly Ala Gly Ala Gly Ser Gly Ala Gly
            260                 265                 270
```

```
Ala Gly Ser Gly Ala Gly Ala Gly Ser Gly Ala Gly Ser Gly
            275                 280                 285

Ala Gly Ala Gly Ser Gly Ala Gly Ala Gly Ser Gly Ala Ala Val Thr
            290                 295                 300

Gly Arg Gly Asp Ser Pro Ala Ser Ala Ala Gly Tyr Gly Ala Gly Ala
305                 310                 315                 320

Gly Ser Gly Ala Gly Ala Gly Ser Gly Ala Gly Ala Gly Ser Gly Ala
            325                 330                 335

Gly Ala Gly Ser Gly Ala Gly Ala Ser Gly Ala Gly Ala Gly Ser
            340                 345                 350

Gly Ala Gly Ala Gly Ser Gly Ala Gly Ala Gly Ser Gly Ala Gly Ala
            355                 360                 365

Gly Ser Arg Lys Leu Pro Asp Ala Gly Ala Gly Ala Gly Ser Gly Ala
            370                 375                 380

Gly Ala Gly Ser Gly Ala Gly Ala Gly Ser Gly Ala Gly Ala Gly Ser
385                 390                 395                 400

Gly Ala Gly Ala Gly Ser Gly Ala Gly Ala Gly Ser Gly Ala Gly Ala
            405                 410                 415

Gly Ser Gly Ala Gly Ala Gly Ser Gly Ala Gly Ala Gly Ser Gly Ala
            420                 425                 430

Ala Val Thr Gly Arg Gly Asp Ser Pro Ala Ser Ala Ala Gly Tyr Gly
            435                 440                 445

Ala Gly Ala Gly Ser Gly Ala Gly Ala Gly Ser Gly Ala Gly Ala Gly
            450                 455                 460

Ser Gly Ala Gly Ala Gly Ser Gly Ala Gly Ala Gly Ser Gly Ala Gly
465                 470                 475                 480

Ala Gly Ser Gly Ala Gly Ala Gly Ser Gly Ala Gly Ala Gly Ser Gly
            485                 490                 495

Ala Gly Ala Gly Ser Arg Lys Leu Pro Asp Ala Gly Ala Gly Ala Gly
            500                 505                 510

Ser Gly Ala Gly Ala Gly Ser Gly Ala Gly Ala Gly Ser Gly Ala Gly
            515                 520                 525

Ala Gly Ser Gly Ala Gly Ala Gly Ser Gly Ala Gly Ala Gly Ser Gly
            530                 535                 540

Ala Gly Ala Gly Ser Gly Ala Gly Ala Gly Ser Gly Ala Gly Ala Gly
545                 550                 555                 560

Ser Gly Ala Ala Val Thr Gly Arg Gly Asp Ser Pro Ala Ser Ala Ala
                    565                 570                 575

Gly Tyr Gly Ala Gly Ala Gly Ser Gly Ala Gly Ala Gly Ser Gly Ala
            580                 585                 590

Gly Ala Gly Ser Gly Ala Gly Ala Gly Ser Gly Ala Gly Ala Gly Ser
            595                 600                 605

Gly Ala Gly Ala Gly Ser Gly Ala Gly Ala Gly Ser Gly Ala Gly Ala
            610                 615                 620

Gly Ser Gly Ala Gly Ala Gly Ser Arg Lys Leu Pro Asp Ala Gly Ala
625                 630                 635                 640

Gly Ala Gly Ser Gly Ala Gly Ala Gly Ser Gly Ala Gly Ala Gly Ser
            645                 650                 655

Gly Ala Gly Ala Gly Ser Gly Ala Gly Ala Gly Ser Gly Ala Gly Ala
            660                 665                 670

Gly Ser Gly Ala Gly Ala Gly Ser Gly Ala Gly Ala Gly Ser Gly Ala
            675                 680                 685

Gly Ala Gly Ser Gly Ala Ala Val Thr Gly Arg Gly Asp Ser Pro Ala
```

```
                       690                 695                 700
Ser Ala Ala Gly Tyr Gly Ala Gly Ala Gly Ser Gly Ala Gly Ala Gly
705                 710                 715                 720

Ser Gly Ala Gly Ala Gly Ser Gly Ala Gly Ala Gly Ser Gly Ala Gly
                725                 730                 735

Ala Gly Ser Gly Ala Gly Ala Gly Ser Gly Ala Gly Ala Gly Ser Gly
            740                 745                 750

Ala Gly Ala Gly Ser Gly Ala Gly Ala Gly Ser Arg Lys Leu Pro Asp
            755                 760                 765

Ala Gly Ala Gly Ala Gly Ser Gly Ala Gly Ala Gly Ser Gly Ala Gly
        770                 775                 780

Ala Gly Ser Gly Ala Gly Ala Gly Ser Gly Ala Gly Ala Gly Ser Gly
785                 790                 795                 800

Ala Gly Ala Gly Ser Gly Ala Gly Ala Gly Ser Gly Ala Gly Ala Gly
                805                 810                 815

Ser Gly Ala Gly Ala Gly Ser Gly Ala Gly Ala Gly Ser Gly Ala Gly
            820                 825                 830

Ala Gly Ser Gly Ala Gly Ala Met Asp Pro Gly Arg Tyr Gln Leu Ser
            835                 840                 845

Ala Gly Arg Tyr His Tyr Gln Leu Val Trp Cys Gln Lys
        850                 855                 860
```

CELL ADHESIVE MATERIAL FOR BIOLOGICAL TISSUE

TECHNICAL FIELD

The present invention relates to a cell-adhesive material for biological tissues.

BACKGROUND ART

Currently, many types of materials for biological tissues each retaining an anti-bacterial activity and an antithrombogenicity, such as artificial joints and artificial dental roots, have been used in the medical and dental fields. As raw materials for the materials for biological tissues, titanium, a titanium alloy, a Co—Cr alloy (vitallium, etc.), stainless steel and tantalum have been used generally. However, these raw materials themselves are less compatible with biological tissues and are inert, and therefore the raw materials have such problems that the adhesiveness of the raw materials to cells and the proliferation of cells are remarkably poor, the adhesion strengths between the materials for biological tissues and biological tissues are insufficient, infection may occur on interfaces between the materials for biological tissues and biological tissues, and the like.

For the purpose of solving the problems, it has been conducted to coat a material for biological tissues with a cell adhesion factor, a cell regulation factor or the like. For example, a material produced by bonding a collagen or the like onto a material for biological tissues through a chemical bond (Patent Document 1), and a material produced by coating a material for biological tissues with laminin or the like through immersing (Patent Document 2) are known.

PRIOR ART DOCUMENTS

Patent Documents

Patent Document 1: JP 2007-051127 A
Patent Document 2: JP 2005-021208 A

DISCLOSURE OF THE INVENTION

Problems to be Solved by the Invention

However, when a cell adhesion factor or a cell regulation factor is immobilized on a material for biological tissues through a chemical bond, there are such problems that the physiological activity of the cell adhesion factor, cell regulation factor or the like is deteriorated and the bonding amount of the cell adhesion factor or the cell regulation factor is insufficient. Further, there is also such a problem that this chemical bonding method requires many steps for modifying the surface of a metal and is therefore complicated. Furthermore, there is such a problem that when the coating is carried out through physical adsorption by immersing or the like, the bonding force between the cell adhesion factor or the cell regulation factor and the material for biological tissues is insufficient and the removal or detachment of the cell adhesion factor or the cell regulation factor occurs.

The problems on the adhesiveness to cells and the proliferation of cells are particularly serious problems in the dental field. In the dental field, from the viewpoints of in vivo stability and biocompatibility, titanium and a titanium alloy have been used mainly as a material for biological tissues such as an artificial dental root or a dental implant. As for a dental implant, a portion of the dental implant is exposed in an oral cavity. Therefore, when the bonding between the dental implant and a gingival epithelial tissue is fragile, it causes a periodontal disease, and as a result, such a problem may often occur that it becomes difficult to maintain the implant for a long period. However, the reality is that any effective means for solving the problem has not been found yet. In addition, when the implant is to be bonded to bone tissues, there is a room for improving the adhesiveness of the implant to cells and the proliferation of cells.

An object of the present invention is to provide a cell-adhesive material for biological tissues, in which the surface of a material for biological tissues (particularly, metallic material) is modified strongly with a large amount of a cell-adhesive artificial peptide (P) that retains a biological activity.

Means for Solving the Problem

The present invention provides a cell-adhesive material for biological tissues comprising a cell-adhesive artificial peptide (P) and a material for biological tissues, wherein the cell-adhesive artificial peptide (P) is immobilized on the surface of the material for biological tissues through an electrochemical reaction.

Advantages of the Invention

A cell-adhesive material for biological tissues according to the present invention has such effects that the adhesiveness to cells is high and the cell proliferation activity is excellent.

MODE FOR CARRYING OUT THE INVENTION

A cell-adhesive artificial peptide (P) can be artificially produced, and can be produced readily by an organic synthesis method (enzyme method, solid-phase synthesis method, liquid-phase synthesis method, etc.), gene recombination or the like. With respect to the organic synthesis method, the methods described in "biochemical experiment course 1, chemistry of proteins IV (edited by the Japan Society of Biochemistry, published by Tokyo Kagaku Dozin Co., Ltd., Jul. 1, 1981)", "continuation biochemistry experiment course 2, chemistry of proteins (part 2), (edited by the Japan Society of Biochemistry, published by Tokyo Kagaku Dozin Co., Ltd., May 20, 1987)", and the like can be applied. With respect to the gene recombination, the methods described in JP 3338441 B (corresponding PCT application: WO 90/05177 pamphlet; the disclosed contents of which are incorporated herein by reference) and the like can be applied. Although both the organic synthesis method and the gene recombination can produce the cell-adhesive artificial peptide (P), the gene recombination is preferred from such viewpoints that amino acids for the cell-adhesive artificial peptide (P) can be designed and altered readily and the cell-adhesive artificial peptide (P) can be produced in a large amount at a low price.

The term "adhesiveness to cells" refers to such a property that a specific minimal amino acid sequence is recognized by integrin receptors in cells and the cells adhere to a base material readily (the Journal of Osaka medical center and research institute of maternal and child health, Vol. 8, No. 1, pp. 58-66, 1992).

From the viewpoint of the exclusion of any animal-derived ingredients, it is preferred that the cell-adhesive artificial peptide (P) is a peptide that is synthesized by a genetic recombinant microorganism and has at least one cell-adhesive minimal amino acid sequence (X) in one molecule. As the cell-adhesive minimal amino acid sequence (X), for example, the sequences described in "pathologic physiology, vol. 9, No. 7, pp. 527-535, 1990", "the Journal of Osaka medical center and research institute of maternal and child health, Vol. 8, No. 1, pp. 58-66, 1992", and the like are used.

Among these minimal amino acid sequences (X), at least one sequence selected from the group consisting of an RGD sequence (SEQ ID NO: 1), an LDV sequence (SEQ ID NO: 2), an LRE sequence (SEQ ID NO: 10), an HAV sequence (SEQ ID NO: 12), an REDV sequence (SEQ ID NO: 3), a YIGSR sequence (SEQ ID NO: 4), a PDSGR sequence (SEQ ID NO: 5), an RYVVLPR sequence (SEQ ID NO: 6), an LGTIPG sequence (SEQ ID NO: 7), an RNIAEIIKDI sequence (SEQ ID NO: 8), an IKVAV sequence (SEQ ID NO: 9), a DGEA sequence (SEQ ID NO: 11), a GVKGDKGNPGWPGAP sequence (SEQ ID NO: 13), a GEFYFDLRLKGDK sequence (SEQ ID NO 14), a YKLNVNDS sequence (SEQ ID NO: 15), an AKPSYPPTYK sequence (SEQ ID NO: 16), an NRWHSIYITRFG sequence (SEQ ID NO: 17), a TWYKIAFQRNRK sequence (SEQ ID NO 18), an RKRLQVQLSTRT sequence (SEQ ID NO: 19) and a PHSRN sequence (SEQ ID NO: 20), where each of the amino acids is expressed by a one-letter code, is preferred. From the viewpoint of the adhesiveness to cells, at least one sequence selected from the group consisting of an RGD sequence (SEQ ID NO: 1), an LDV sequence (SEQ ID NO: 2), an LRE sequence (SEQ ID NO 10), an HAV sequence (SEQ ID NO: 12), an REDV sequence (SEQ ID NO: 3), a YIGSR sequence (SEQ ID NO: 4), a PDSGR sequence (SEQ ID NO: 5), an RYVVLPR sequence (SEQ ID NO: 6), an LGTIPG sequence (SEQ ID NO: 7), an RNIAEIIKDI sequence (SEQ ID NO: 8), an IKVAV sequence (SEQ ID NO: 9) and a DGEA sequence (SEQ ID NO: 11) is more preferred, and at least one sequence selected from the group consisting of an RGD sequence (SEQ ID NO: 1), a YIGSR sequence (SEQ ID NO: 4) and an IKVAV sequence (SEQ ID NO: 9) is particularly preferred.

From the viewpoint of the adhesiveness to cells, the cell-adhesive artificial peptide (P) preferably has at least one cell-adhesive minimal amino acid sequence (X) in one molecule, more preferably 3 to 50 sequences in one molecule, still more preferably 4 to 30 sequences in one molecule, particularly preferably 5 to 20 sequences in one molecule, and most preferably 13 sequences in one molecule.

From the viewpoint of the stability to heat, the cell-adhesive artificial peptide (P) preferably contains an auxiliary amino acid sequence (Y), in addition to the cell-adhesive minimal amino acid sequences. Examples of the auxiliary amino acid sequence (Y) include a GAGAGS sequence (SEQ ID NO: 21) and the like. When the auxiliary amino acid sequence (Y) is contained, from the viewpoint of the stability to heat, the content of the auxiliary amino acid sequence (Y) is at least two sequences, more preferably 3 to 10,000 sequences, particularly preferably 10 to 3,000 sequences, and most preferably 30 to 1,000 sequences in one molecule of the cell-adhesive artificial peptide (P). From the viewpoint of thermal stability, it is preferred that the auxiliary amino acid sequence (Y) is contained in a contiguously repeated form, i.e., $(Y)_a$ (wherein a represents an arbitrary integer), and an example thereof includes $(GAGAGS)_a$ (wherein a represents an arbitrary integer). From the viewpoint of productivity, the preferred range of a, i.e., the number of repetition, is 2 to 33, more preferably 3 to 23, and particularly preferably 4 to 13.

When the cell-adhesive artificial peptide (P) contains the cell-adhesive minimal amino acid sequences (X) and the auxiliary amino acid sequences (Y), the ratio of the number of the cell-adhesive minimal amino acid sequences (X) to the number of the auxiliary amino acid sequences (Y) in the cell-adhesive peptide (P), i.e., [(X)/(Y)], is preferably 0.002 to 10, more preferably 0.01 to 2, and particularly preferably 0.05 to 0.5, from the viewpoints of the adhesiveness to cells and the stability to heat. Further, from such a viewpoint that a β-sheet structure of the cell-adhesive artificial peptide (P) can be facilitated, it is preferred that the cell-adhesive minimal amino acid sequences (X) and the auxiliary amino acid sequences (Y) are arranged alternately.

From such a viewpoint that a large amount of the cell-adhesive artificial peptide (P) can modify the surface of the material for biological tissues strongly, it is preferred that the cell-adhesive artificial peptide (P) has a residue of an amino acid having an amino group and/or a carboxyl group in a side chain thereof. Examples of the amino acid having an amino group in a side chain thereof include arginine (Arg), asparagine (Asn), histidine (His) and glutamine (Gln). Examples of the amino acid having a carboxyl group in a side chain thereof include aspartic acid (Asp) and glutamic acid (Glu).

The cell-adhesive artificial peptide (P) may be further modified with a compound (AM). Examples of the compound (AM) include a compound (salt) (AM-1) containing a primary amino group, a secondary amino group, a tertiary amino group and/or a quaternary ammonio group, a compound (AM-2) containing a carboxyl group, a compound (AM-3) containing a sulfo group, and a compound (AM-4) containing a hydroxyl group. When the cell-adhesive artificial peptide (P) is modified with the compound (AM), the adhesiveness of the cell-adhesive material for biological tissues according to the present invention to cells can be further improved and the material for biological tissues can be modified with a larger amount of the cell-adhesive artificial peptide (P) more strongly.

As the compound (salt) (AM-1) containing a primary amino group, a secondary amino group, a tertiary amino group and/or a quaternary ammonio group, a polyamine, an amino alcohol, a halide having an amino group, an amino group-containing monomer and a polymer composed of, as a constituent monomer, an amino group-containing monomer, as well as salts or quaternized products thereof, and the like can be used.

As the polyamine, a polyamine having at least one primary amino group or secondary amino group (2 to 56 carbon atoms) and the like are used, and an aliphatic polyamine, an alicyclic polyamine, a heterocyclic polyamine, an aromatic polyamine, and the like are used.

Examples of the aliphatic polyamine include alkylenediamines (ethylenediamine, propylenediamine, trimethylenediamine, tetramethylenediamine, hexamethylenediamine, etc.), polyalkylene polyamines having an alkylene group with 2 to 6 carbon atoms (diethylenetriamine, iminobispropylamine, triethylenetetramine, tetraethylenepentamine, pentaethylenehexamine, etc.), alkyl (1 to 18 carbon atoms)-substituted products thereof (dimethylaminopropylamine, diethylaminopropylamine, dipropylaminopropylamine, methylethylaminopropylamine, trimethylhexamethylenediamine, N,N-dioctadecylethylenediamine, trioctadecylethylenediamine, methyliminobispropylamine, etc.), and the like.

Examples of the alicyclic polyamine include 1,3-diaminocyclohexane, 1,3-bis(methylamino)cydohexane, 1,3-bis(dihydroxyamino)cydohexane, isophoronediamine, menthanediamine, 4,4'-methylenedicydohexanediamine, and the like.

Examples of the heterocyclic polyamine include piperazine, N-methylpiperazine, N-aminoethylpiperazine, 1,4-diaminoethylpiperazine, and the like.

Examples of the aromatic polyamine include phenylenediamine, N,N'-dimethylphenylenediamine, N,N,N'-trimethylphenylenediamine, diphenylmethanediamine, 2,6-diaminopyridine, tolylenediamine, diethyltolylenediamine, 4,4'-bis(methylamino)diphenylmethane, 1-methyl-2-methylamino-4-aminobenzene, and the like.

As the amino alcohol, an amino alcohol having 2 to 58 carbon atoms and the like can be used, and examples thereof include alkanol amines having 2 to 10 carbon atoms [monoethanolamine, diethanolamine, triethanolamine, monoisopropanolamine, monobutanolamine, triethanolamine, tripropanolamine, tributanolamine, N,N-bis(hydroxyethyl)ethylenediamine, N,N,N',N'-tetrakis(hydroxyethyl)ethylenediamine, etc.], alkyl (1 to 18 carbon atoms)-substituted products thereof [N,N-dimethylethanolamine, N,N-diethylethanolamine, N-ethyldiethanolamine, N-octadecyldiethanolamine, N,N-diethyl-N',N'-bis(hydroxyethyl)ethylenediamine, N,N-dioctadecyl-N',N'-bis(hydroxyethyl)ethylenediamine, N,N,N'-trioctadecyl-N'-hydroxyethylethylenediamine, etc.], and the like.

Examples of the halide having an amino group include a halogenated (chlorinated, brominated, etc.) product of an alkyl amine having 2 to 17 carbon atoms and the like, and examples thereof include aminoethyl chloride, N-methylaminopropyl chloride, dimethylaminoethyl chloride, diethylaminoethyl chloride, dibenzylaminoethyl bromide, dimethylaminopropyl bromide, diethylaminopropyl chloride, dibenzylaminopropyl chloride, and the like.

As the amino group-containing monomer, an amino group-containing vinyl compound having 5 to 21 carbon atoms, ethyleneimine, an amino acid having 2 to 20 carbon atoms, and the like are used.

As the amino group-containing vinyl compound, amino group-containing (meth)acrylate, amino group-containing (meth)acrylamide, amino group-containing aromatic vinyl hydrocarbon, amino group-containing allyl ether, and the like are used.

Examples of the amino group-containing (meth)acrylate include aminoethyl(meth)acrylate, N-methylaminoethyl(meth)acrylate, N,N-dimethylaminoethyl(meth)acrylate, N,N-diethylaminopropyl(meth)acrylate, N,N-dipropylaminoethyl(meth)acrylate, N-benzyl-N-methylaminoethyl(meth)acrylate, N,N-dibenzylaminoethyl(meth)acrylate, N,N-dibenzylaminopropyl(meth)acrylate, morpholinoethyl(meth)acrylate, N-methylpiperidinoethyl(meth)acrylate, and the like.

Examples of the amino group-containing (meth)acrylamide include aminoethyl acrylamide, N-methylaminopropyl acrylamide, N,N-dimethylaminoethyl(meth)acrylamide, N,N-diethylaminopropyl(meth)acrylamide, N,N-dipropylaminoethyl(meth)acrylamide, N-benzyl-N-methylaminoethyl(meth)acrylamide, morpholinoethyl(meth)acrylamide, N-methylpiperidinoethyl(meth)acrylamide, and the like.

Examples of the amino group-containing aromatic vinyl hydrocarbon include aminoethylstyrene, N-methylaminoethylstyrene, N,N-dimethylaminostyrene, N,N-dipropylaminostyrene, N-benzyl-N-methylaminostyrene, and the like.

Examples of the amino group-containing allyl ether include aminoethyl allyl ether, N-methylaminoethyl allyl ether, N,N-dimethylaminoethyl allyl ether, N,N-diethylaminoethyl allyl ether, and the like.

Examples of the amino acid include arginine, histidine, isoleucine, leucine, methionine, phenylalanine, threonine, tryptophan, tyrosine, valine, alanine, asparagine, aspartic acid, glutamine, glutamic acid, proline, cysteine, lysine, serine, glycine, 3-aminopropionic acid, 8-aminooctanoic acid, 20-aminoeicosanoic acid, and the like.

Examples of the polymer of an amino group-containing monomer include a vinyl polymer which contains an amino group-containing vinyl compound as an essential constituent monomer, polyethyleneimine, a polypeptide (excluding the cell-adhesive artificial polypeptide (P)), and the like.

The polymer of an amino group-containing monomer has a weight average molecular weight of preferably 500 to 1,000,000, more preferably 1,000 to 800,000, and particularly preferably 2,000 to 500,000. The weight average molecular weight can be measured by gel permeation chromatography (GPC) {standard substance: a polystyrene standard having a molecular weight of 420 to 20,600,000 (manufactured by Tosoh Corporation), etc.}.

Examples of the salts thereof include inorganic salts (a hydrochloric acid salt, a nitric acid salt, a perchloric acid salt, etc.) of amines thereof (a polyamine, an amino alcohol, a halide having an amino group, an amino group-containing monomer, and a polymer containing an amino group-containing monomer as a constituent monomer), and the like.

Examples of the quaternized products thereof include quaternized products produced by quaternizing these amines with a quaternizing agent (methyl chloride, ethyl chloride, benzyl chloride, dimethyl carbonate, dimethyl sulfate, ethylene oxide, etc.), and the like.

Among these compounds (salts) (AM-1) each containing a (primary to tertiary) amino group and/or a quaternary ammonio group, from the viewpoint of the adhesiveness to cells, a halide having an amino group and a salt thereof are preferred, N,N-dimethylaminoethyl chloride hydrochloride, dimethylaminoethyl chloride and diethylaminoethyl chloride are more preferred, and dimethylaminoethyl chloride is particularly preferred.

Examples of the compound (AM-2) containing a carboxyl group include a carboxylic acid having 1 to 30 carbon atoms and a halogen-substituted carboxylic acid having 2 to 30 carbon atoms.

Examples of the carboxylic acid having 1 to 30 carbon atoms include formic acid, acetic acid, propionic acid, succinic acid, glycolic acid, gluconic acid, lactic acid, malic acid, tartaric acid, citric acid, ascorbic acid, glucuronic acid, maleic acid, fumaric acid, pyruvic acid, aspartic acid, glutamic acid, benzoic acid, anthranilic acid, mesylic acid, salicylic acid, 4-hydroxybenzoic acid, phenylacetic acid, tricosanoic acid, and the like.

Examples of the halogen-substituted carboxylic acid having 1 to 30 carbon atoms include 3-chloropropionic acid, p-chlorobenzoic acid, ω-bromotricosanoic acid and chloroformic acid.

Among these compounds (AM-2) each containing a carboxyl group, from the viewpoint of the adhesiveness to cells, a halogen-substituted carboxylic acid is preferred, and chloroacetic acid is more preferred.

Examples of the compound (AM-3) containing a sulfo group include a sulfonic acid having 2 to 30 carbon atoms and a halogen-substituted sulfonic acid having 2 to 30 carbon atoms.

Examples of the sulfonic acid having 2 to 30 carbon atoms include ethanesulfonic acid, benzenesulfonic acid, pantothenic acid, 2-hydroxyethanesulfonic acid, toluenesulfonic acid, sulfanilic acid, cyclohexylaminosulfonic acid, tricosanesulfonic acid, and the like.

Examples of the halogen-substituted sulfonic acid having 2 to 30 carbon atoms include chlorosulfonic acid, chloroethanesulfonic acid, 3-bromopropanesulfonic acid, p-chlorobenzenesulfonic acid, ω-bromotricosanesulfonic acid.

Among these compounds (AM-3) each having a sulfo group, from the viewpoint of the adhesiveness to cells, a halogen-substituted sulfonic acid is preferred, and chloroethanesulfonic acid is more preferred.

Examples of the compound (AM-4) containing a hydroxyl group include an alcohol having 1 to 4 carbon atoms and a hydroxyl group-containing halide having 1 to 4 carbon atoms.

Examples of the alcohol having 1 to 4 carbon atoms include methanol, ethanol, propanol, butanol, t-butanol, and the like.

Examples of the hydroxyl group-containing halide include chloroethanol, chloropropanol, bromomethanol, 4-chlorobutanol, and the like.

Among these compounds (AM-4) containing a hydroxyl group, from the viewpoint of the adhesiveness to cells, a hydroxyl group-containing halide is preferred, and chloroethanol is more preferred.

As the method for modifying with the compound (AM), (1) a method of chemically bonding the compound (AM) to a cell-adhesive artificial peptide (P') before modification {covalent bond, ionic bond and/or hydrogen bond, etc.}, (2) a method of physically adsorbing the compound (AM) onto a cell-adhesive artificial peptide (P') before modification (adsorption by means of Van der Wags force), and the like can be applied.

Among these methods, from the viewpoint of bonding strength, (1) the chemically bonding method is preferred, and the method (1) in which a covalent bond is carried out is more preferred.

When (1) the compound (AM) is chemically bonded to the cell-adhesive artificial peptide (P') before modification {covalent bond, ionic bond and/or hydrogen bond, etc.}, it is preferred that the cell-adhesive artificial peptide (P') before modification contains an amino acid residue having a reactive group {hydroxyl group, carboxyl group, mercapto group, primary or secondary amino group, etc.}. Among these reactive groups, from the viewpoint of easiness of chemical bond formation, a hydroxyl group, a carboxyl group and a primary amino group are preferred, a hydroxyl group and a carboxyl group are more preferred, and a hydroxyl group is particularly preferred. Examples of the amino acid residue having a reactive group include the above-mentioned amino acid residues each containing an amino group and/or a carboxyl group in a side chain thereof.

When the cell-adhesive artificial peptide (P') before modification contains an amino acid residue having a reactive group, at least one of the reactive groups may be contained in one molecule of the cell-adhesive artificial peptide (P') before modification. From the viewpoint of the bondability to the material for biological tissues (for the purpose of modifying the material for biological tissues with a larger amount of the cell-adhesive artificial peptide (P) more strongly), the number of the reactive groups is 2 to 50 in one molecule, more preferably 3 to 30 in one molecule, and particularly preferably 5 to 20 in one.

As the method of a chemical bond, any known method can be applied, and examples thereof include the methods described in Patent Document 1 (JP 2007-51127 A) and the like. In the reaction for chemical bond formation, a reaction solvent may be used, and any known reaction solvent can be used as the reaction solvent, and examples thereof include water, an aqueous lithium bromide solution, an aqueous lithium perchlorate solution, methanol, ethanol, isopropanol, acetone, dimethyl sulfoxide, dimethyl acetamide and tetrahydrofuran.

Specific examples of a method of bonding the compound (AM) to the cell-adhesive artificial peptide (P') before modification through a covalent bond include: in the case where the cell-adhesive artificial peptide (P') before modification has an amino acid residue containing a hydroxyl group in a side chain thereof (e.g., Ser and Tyr), a method of reacting the cell-adhesive artificial peptide (P') before modification with a halide having an amino group, a halogen-substituted carboxylic acid, a halogen-substituted sulfonic acid or a hydroxyl group-containing halide among the compounds (AM) (Williamson synthesis method) to form an ether bond; in the case where the cell-adhesive artificial peptide (P') before modification has an amino acid residue having a carboxyl group in a side chain thereof (e.g., Asp and Glu), a method of reacting the cell-adhesive artificial peptide (P') before modification with an amino alcohol among the compound (AM) to form an ester bond; and the like.

Preferred examples of the cell-adhesive artificial peptide (P) are as follows:

a peptide (SEQ ID NO: 23) which has a structure composed of 13 RGD sequences (SEQ ID NO: 1) and 12 (GAGAGS)$_9$ sequences (SEQ ID NO: 22) arranged alternately and has a number average molecular weight (Mn) of about 110,000 {"Pronectin F", Pronectin is a registered trademark by Sanyo Chemical Industries, Ltd. (in Japan and U.S.A.), manufactured by Sanyo Chemical Industries, Ltd. <the same shall apply hereinafter>};

a peptide (SEQ ID NO: 25) which has a structure composed of five RGD sequences (SEQ ID NO: 1) and five (GAGAGS)$_3$ sequences (SEQ ID NO: 24) arranged alternately and has an Mn of about 20,000 ("Pronectin F2");

a peptide (SEQ ID NO: 26) which has a structure composed of three RGD sequences (SEQ ID NO: 1) and three (GAGAGS)$_3$ sequences (SEQ ID NO: 24) arranged alternately and has an Mn of about 10,000 ("Pronectin F3");

a peptide (SEQ ID NO: 28) which has a structure composed of six RGD sequences (SEQ ID NO: 1), six RKLPDA sequences (SEQ ID NO: 27) and 12 (GAGAGS)$_9$ sequences (SEQ ID NO: 22) arranged alternately in the order of the RGD sequence (SEQ ID NO: 1), the (GAGAGS)$_9$ sequence (SEQ ID NO: 22), the RKLPDA sequence (SEQ ID NO: 27) and the (GAGAGS)$_9$ sequence (SEQ ID NO: 22) and has an Mn of about 110,000 ("Pronectin FT");

a peptide that is obtained by chemically bonding an amino acid sequence, i.e., an RKLPDA sequence (SEQ ID NO: 27), to a Ser residue in "Pronectin F" and has an Mn of about 120,000 ("Pronectin FT2"); and the like.

From the viewpoint of the adhesiveness to cells, the bondability to the material for biological tissues and the stability to heat, the cell-adhesive artificial peptide (P) has a number average molecular weight (Mn) of preferably 300 to 3,000,000, more preferably 1,000 to 1,000,000, and particularly preferably 3,000 to 300,000. The number average molecular weight (Mn) of the cell-adhesive artificial peptide (P) can be determined by separating the cell-adhesive artificial peptide (P) by an SDS-PAGE (SDS polyacrylamide gel electrophoresis) method and then comparing the migration distance of the separated cell-adhesive artificial peptide (P) with that of a standard substance.

It is considered that the electrochemical reaction for immobilizing the cell-adhesive artificial peptide (P) onto the surface of the material for biological tissues is a reaction in which an electrochemical potential is altered by other external factors in an electrochemical system and which progresses through processes such as the migration of a substance toward the surface of an electrode, the adsorption of the substance onto the surface of the electrode, the dissociation of the substance on the surface of the electrode, the acceptance of an electron, and the like. That is, it is considered that a proton is added to the amino group in the cell-adhesive artificial peptide (P) to produce an ammonium cation, the ammonium cation migrates toward a cathode, the ammonium cation is adsorbed on the surface of the cathode and then dissociated into an amino group and a proton on the surface of the cathode, and an electron is given to the proton by the cathode, thereby generating hydrogen gas. Meanwhile, it is also considered that an electron in a lone electron pair of the amino group is shared with a free electron of a metal serving as the cathode, whereby a strong bond is formed between the amino group in the cell-adhesive artificial peptide (P) and the material for biological tissues serving as the cathode, and the strong bond is maintained after the termination of flowing electricity.

As a method of producing the cell-adhesive material for biological tissues according to the present invention, for example, a method can be applied in which a material for biological tissues and an electrode are immersed in a solution having a cell-adhesive artificial peptide (P) dissolved therein, the material for biological tissues is used as a cathode, the electrode is used as an anode, and a voltage (electric charge) is applied to both of the electrodes, thereby immobilizing the cell-adhesive artificial peptide (P) onto the surface of the material for biological tissues through an electrochemical reaction.

A solvent for dissolving the cell-adhesive artificial peptide (P) is not particularly limited, as long as the solvent can dissolve the cell-adhesive artificial peptide (P) therein at a concentration of 1 ng/ml or more. Examples thereof include water, methanol, ethanol, dimethyl sulfoxide, an aqueous perchlorate solution (aqueous lithium perchlorate solution, etc.), and the like, and from the viewpoint of the affinity for cells, water and an aqueous perchlorate solution are preferred.

It is preferred that an inorganic electrolyte is dissolved in the solvent for dissolving the cell-adhesive artificial peptide (P). As the inorganic electrolyte to be dissolved, a chloride of an alkali metal or an alkali earth metal can be used, and examples thereof include sodium chloride, potassium chloride, calcium chloride, and the like. When the inorganic electrolyte is dissolved in the solvent, the solution of the cell-adhesive artificial peptide (P) can have electrical conductivity, the progress of the electrochemical reaction is easily facilitated by the application of an electric charge, and at the same time, the migration of the cell-adhesive artificial peptide (P) toward the material for biological tissues is easily facilitated. When the inorganic electrolyte is used, the inorganic electrolyte has a concentration of preferably 1 to 5 wt %, and more preferably 2 to 4 wt %, based on the weight of the solvent. When the concentration falls within this range, the electrical conductivity of the aqueous solution can be further improved, and the adsorption of ions derived from the inorganic electrolyte onto the surface of the metal can be prevented.

From the viewpoint of easiness of progression of the electrochemical reaction, the cell-adhesive artificial peptide (P) has a concentration of preferably 0.1 to 1000 μg/ml, and more preferably 1 to 100 μg/ml, based on the volume of the solution of the cell-adhesive artificial peptide (P). When the concentration falls within this range, the bonding amount of the cell-adhesive artificial peptide (P) becomes more satisfactory, and more sufficient adhesiveness to cells and more sufficient proliferation of cells are achieved.

The voltage to be applied between the cathode (material for biological tissues) and the anode is preferably 0.1 to 10 V, and more preferably 1 to 7 V. When the voltage falls within this range, a more uniform coating film {coating film composed of the cell-adhesive artificial peptide (P)} can be formed, and the time required for the formation of the coating film can be further reduced.

A current density to be applied is preferably $1 \times 10^{-7}$ to $5 \times 10^{-5}$ A/dm$^2$, and more preferably $5 \times 10^{-8}$ to $1 \times 10^{-5}$ A/dm$^2$, based on the surface area of the cathode. When the current density falls within this range, a more uniform coating film {coating film composed of the cell-adhesive artificial peptide (P)} can be formed, and the time required for the formation of the coating film can be further reduced.

Examples of the cells that can adhere onto the cell-adhesive material for biological tissues according to the present invention include an insect cell, a plant cell and an animal cell. Among these cells, from the viewpoint of the adhesiveness to cells, an animal cell is preferred, and a mammalian cell is particularly suitable. Examples of a mammal include mammals described in Dictionary on Biology [published by Iwanami Shoten, Publishers, 1969), such as Marsupialia (kangaroo, etc.), Primates (monkey, chimpanzee, human, etc.), Simplicidentata (squirrel, mouse, hedgehog, etc.), Cetacea (dolphin, killer whale, whale, etc.), Carnivora (dog, fox, bear, cat, lion, tiger, etc.), Perissodactyla (horse, donkey, rhino, etc.), and Artiodactyla (boar, pig, camel, deer, cow, goat, sheep, etc.). Among the mammals, human, dog, cat, horse, cow and pig are preferred, and human is more preferred. Examples of the mammalian cell include cells associated with blood vessels (vascular endothelial cell, smooth muscle cell, fibroblast, etc.), cells associated with muscles (muscle cell, etc.), cells associated with fats (adipocyte, etc.), cells associated with nerves (nerve cell, etc.), cells associated with the liver (hepatic parenchymal cell, etc.), cells associated with the pancreas (pancreatic islet cell, etc.), cells associated with the kidney (renal epithelial cell, renal proximal tubule epithelial cell, mesangial cell, etc.), cells associated with the lung or bronchial tube (epithelial cell, fibroblast, vascular endothelial cell and smooth muscle cell), cells associated with eyes (photoreceptor cell, corneal epithelial cell, corneal endothelial cell, etc.), cells associated with the prostate (epithelial cell, stromal cell and smooth muscle cell), cells associated with bones (osteoblast, bone cell, osteoclast, etc.), cells associated with cartilages (chondroblast, chondrocyte, etc.), cells associated with teeth (periodontal ligament cell, pulp cell, ameloblast, odontoblast, enamel cell and odontocyte), and stems cells thereof. Among these cells, cells associated with bones (osteoblast, bone cell, osteoclast, etc.), cells associated with cartilages (chondroblast, chondrocyte, etc.), cells associated with teeth or gingiva (periodontal ligament cell, gingival epithelial cell, and osteoblast), and stems cells thereof (mesenchymal stem cell, embryonic stem cell, etc.) are preferred.

Examples of the material for biological tissues include a metal, an electrically conductive ceramic, and the like. Examples of the metal include titanium, iron, stainless steel, zirconium, tantalum, platinum, gold, composite materials composed of two or more of these metals (Transplantation and artificial organs, Iwanami Koza, Basis of modern medicine, vol. 14, published by Iwanami Shoten, Publishers, JP 1995-88174 A, etc.), and the like. Examples of the composite material include a titanium alloy (Ti-6Al-4V, Ti-6Al-2Nb-1Ta, etc.), a cobalt-chromium alloy, and the like.

Examples of the electrically conductive ceramic include titanium borate ($TiB_2$), silicon carbide (SiC), electroconductive zirconia, and the like. From the viewpoint of biocompatibility, titanium and a titanium alloy are preferred.

The shape of the material for biological tissues is not particularly limited, and examples thereof include the shapes described in "Transplantation and artificial organs (Iwanami Koza, Basis of modern medicine, vol. 14), published by Iwanami Shoten, Publishers", such as the shape of an artificial hip joint, the shape of an artificial knee joint, the shape of an artificial dental root, the shape of a bone filler material, and the like.

From the viewpoint of the adhesiveness to cells, the ratio of the area (N) of the material for biological tissues on which the cell-adhesive artificial peptide (P) is immobilized to the surface area (M) of the material for biological tissues {surface area on which cells can be attached} [(ratio of surface area to be coated with cell-adhesive artificial peptide (P))=(N)×100/(M)} is preferably 50 to 100%, and more preferably 80 to 100%.

The ratio of the surface area to be coated with the cell-adhesive artificial peptide (P) is obtained in the following manner: the area (N) of the material for biological tissues on which the cell-adhesive artificial peptide (P) is immobilized is determined by immunochemical staining using an antibody having antibody reactivity with the cell-adhesive artificial peptide (P) {the area (N) is determined by analyzing a photographic image (single-lens reflex camera D70, manufactured by Nikon Corporation, magnification: 10 folds)}, and then the ratio is calculated from the obtained surface area (N) and the surface area (M) of the material for biological tissues {surface area on which cells can be attached}.

From the viewpoint of the adhesiveness to cells, the bonding amount of the cell-adhesive artificial peptide (P) is preferably 0.1 to 1000 $ng/mm^2$, and more preferably 1 to 100 $ng/mm^2$, based on the surface area of the material for biological tissues.

The bonding amount of the cell-adhesive artificial peptide (P) is obtained in the following manner: the cell-adhesive material for biological tissues is immersed in an acidic solution, the cell-adhesive artificial peptide (P) is hydrolyzed into amino acids, the concentration ($\alpha$) (mol/L) of the amino acids in the acidic solution is determined by a TNBS method (2,4,6-trinitrobenzenesulfonic acid absorption spectrophotometry), and the amount is calculated from the concentration ($\alpha$), the number of moles ($\beta$) of the amino acids which constitute 1 mole of the cell-adhesive artificial peptide (P), the molecular weight ($\gamma$) of the cell-adhesive artificial peptide (P) and the surface area (M) of the material for biological tissues {surface area on which cells can be attached} in accordance with the following formula: (bonding amount)={($\alpha/\beta$)×$\gamma$}/M.

The cell-adhesive material for biological tissues according to the present invention has good adhesiveness to various types of cells, and therefore can be used as a material for a medical device that functions in various types of living organisms. From the viewpoint of the adhesiveness to cells, the cell-adhesive material for biological tissues can be used preferably as a base material for an artificial organ, a base material for dental applications, a base material for orthopedic applications and a base material for ophthalmic applications.

The cell-adhesive material for biological tissues according to the present invention is a cell-adhesive material for biological tissues which has good adhesiveness to various types of cells, and is therefore suitable as an implant, a bone fixer, a bone cage, a dental implant, a catheter, a guide wire, a stent and an artificial joint which are medical devices for biological implantation.

EXAMPLES

Hereinafter, the present invention will be described in more detail by way of examples. However, the present invention is not limited thereto.

Example 1

A peptide (SEQ ID NO: 23) which had a structure composed of 13 RGD sequences (SEQ ID NO: 1) and 12 $(GAGAGS)_9$ sequences (SEQ ID NO: 22) arranged alternately and had a number average molecular weight (Mn) of about 110,000 {cell-adhesive artificial peptide (P1-0)} was produced using genetic recombinant *Escherichia coli* in accordance with the method described in examples in JP 1991-502935 A (corresponding PCT application: WO 90/05177 pamphlet; the disclosed contents of which are incorporated herein by reference).

The cell-adhesive artificial peptide (P1-0) (50 mg) and N,N-dimethylaminoethyl chloride hydrochloride (special grade reagent) (150 mg) were dissolved in a 4.5 M aqueous lithium perchlorate solution (1.5 mL) at 20 to 40° C. To the resultant solution was dropwisely added and charged a 4.5 M aqueous lithium perchlorate solution (1.325 mL), in which sodium hydroxide (special grade reagent) (100 mg) had been dissolved, at a certain rate over 45 to 50 seconds while agitating the resultant solution at 20 to 40° C. After agitating at room temperature (25° C.) for 1 hour, the reaction liquid was dialyzed against deionized water (10 L) for 48 hours using a dialysis membrane having a cut-off molecular weight of 12,000 to 14,000. In the dialysis, in first 12 hours, deionized water was replaced by fresh one every 4 hours. The resultant aqueous solution was lyophilized for 24 hours under the conditions of a temperature of −20° C. and a pressure of 0.1 kPa or less, thereby producing a water-soluble cell-adhesive artificial peptide (P1-1).

The number of the molecules of N,N-dimethylaminoethyl chloride hydrochloride introduced thereinto was measured in accordance with the method described in examples in JP 1998-500701 A (corresponding PCT application: WO 96/16168 pamphlet; the disclosed contents of which are incorporated herein by reference), and as a result, it was found that 12 molecules were contained in one molecule of the water-soluble cell-adhesive artificial peptide (P1-1).

An aqueous solution (300 ml) produced by dissolving the cell-adhesive artificial peptide (P1-1) thus produced in a 0.9 wt % aqueous sodium chloride solution in such a manner that the concentration of the cell-adhesive artificial peptide (P1-1) became 5 µg/ml was introduced into a electrolysis vessel made of glass having a height of 200 mm and a bottom surface inner diameter of 135 mm. A (rod-shaped) platinum electrode was used as an anode, a material for biological tissues (titanium plate, rectangular parallelepiped having a size of 100 mm×100 mm×0.1 mm) (manufactured by The Nilaco Corporation) was used as a cathode, and a voltage of 3.0 V was applied between both of the electrodes while agitating the aqueous solution by rotating a stirring bar by means of a magnetic stirrer to flow electricity for 10 minutes, thereby carrying out an electrochemical reaction (current density: $3 \times 10^{-5}$ $A/dm^2$, distance between electrodes: 5 cm, temperature of aqueous solution: 4° C.).

After the termination of flowing electricity, a washing operation involving immersing the titanium plate in deionized water (500 mL) and immediately taking out the titanium plate therefrom was carried out three times, and the titanium plate was then dried for 2 hours in an air circulation dryer at 60° C., thereby producing a cell-adhesive material for biological tissues (A1) according to the present invention in which the cell-adhesive artificial peptide (P1-1) was immobilized on the surface of titanium.

The bonding amount of the cell-adhesive artificial peptide (P1-1) bonded to the cell-adhesive material for biological tissues (A1) was quantified by a known trinitrobenzenesulfonic acid (TNBS) method {biochemical experiment course 1, protein chemistry IV (edited by the Japan Society of Biochemistry, published by Tokyo Kagaku Dozin Co., Ltd., Jul. 1, 1981), etc.}, and as a result, it was found that the bonding amount (J) of the cell-adhesive artificial peptide (P1-1) immediately after the production was 70 ng/mm$^2$.

Example 2

A cell-adhesive material for biological tissues (A2) according to the present invention was produced in the same manner as in Example 1, except that the cell-adhesive artificial peptide (P1-1) was changed to the cell-adhesive artificial peptide (P1-0). The bonding amount (J) of the cell-adhesive artificial peptide (P1-0) bonded to the cell-adhesive material for biological tissues (A2) immediately after the production was 70 ng/mm$^2$.

Example 3

A cell-adhesive artificial peptide (P1-2) was produced in the same manner as in Example 1, except that N,N-dimethylaminoethyl chloride hydrochloride (special grade reagent) was changed to chloroacetic acid (special grade reagent). The number of the molecules of chloroacetic acid introduced into the cell-adhesive artificial peptide (P1-2) was 12 in one molecule of the cell-adhesive artificial peptide (P1-2).

A cell-adhesive material for biological tissues (A3) according to the present invention was produced in the same manner as in Example 1, except that the cell-adhesive artificial peptide (P1-1) was changed to the cell-adhesive artificial peptide (P1-2). The bonding amount (J) of the cell-adhesive artificial peptide (P1-2) bonded to the cell-adhesive material for biological tissues (A3) immediately after the production was 60 ng/mm$^2$.

Example 4

A cell-adhesive material for biological tissues (A4) according to the present invention was produced in the same manner as in Example 1, except that the cell-adhesive artificial peptide (P1-1) was changed to a peptide (P2-0) which had a structure composed of five RGD sequences and five (GAGAGS)$_3$ sequences (SEQ ID NO: 24) arranged alternately and had a number average molecular weight (Mn) of about 20,000 (which was prepared in accordance with the method described in examples in JP 1991-502935 A). The bonding amount (J) of the cell-adhesive artificial peptide (P2-0) bonded to the cell-adhesive material for biological tissues (A4) immediately after the production was 60 ng/mm$^2$.

Example 5

A cell-adhesive artificial peptide (P2-1) was produced in the same manner as in Example 1, except that the cell-adhesive artificial peptide (P1-0) was changed to the cell-adhesive artificial peptide (P2-0). The number of the molecules of N,N-dimethylaminoethyl chloride hydrochloride introduced into the cell-adhesive artificial peptide (P2-1) was six in one molecule of the cell-adhesive artificial peptide (P2-1).

Further, a cell-adhesive material for biological tissues (A5) according to the present invention was produced in the same manner as in Example 1, except that the cell-adhesive artificial peptide (P1-1) was changed to the cell-adhesive artificial peptide (P2-1). The bonding amount (J) of the cell-adhesive artificial peptide (P2-1) bonded to the cell-adhesive material for biological tissues (A5) immediately after the production was 60 ng/mm$^2$.

Example 6

A cell-adhesive material for biological tissues (A6) according to the present invention was produced in the same manner as in Example 1, except that the cell-adhesive artificial peptide (P1-1) was changed to a peptide (P3-0) which had a structure composed of five YIGSR sequences (SEQ ID NO: 4) and five (GAGAGS)$_3$ sequences (SEQ ID NO: 24) arranged alternately and had a number average molecular weight (Mn) of about 20,000 (which was prepared in accordance with the method described in examples in JP 1991-502935 A). The bonding amount (J) of the cell-adhesive artificial peptide (P3-0) bonded to the cell-adhesive material for biological tissues (A6) immediately after the production was 60 ng/mm$^2$.

Example 7

A cell-adhesive material for biological tissues (A7) according to the present invention was produced in the same manner as in Example 1, except that the cell-adhesive artificial peptide (P1-1) was changed to a peptide (P4-0) which had a structure composed of five IKVAV sequences (SEQ ID NO: 9) and five (GAGAGS)$_3$ sequences (SEQ ID NO: 24) arranged alternately and had a number average molecular weight (Mn) of about 20,000 (which was prepared in accordance with the method described in examples in JP 1991-502935 A). The bonding amount (J) of the cell-adhesive artificial peptide (P4-0) bonded to the cell-adhesive material for biological tissues (A7) immediately after the production was 60 ng/mm$^2$.

Comparative Example 1

A comparative cell-adhesive material for biological tissues (B1) was produced in the same manner as in Example 1, except that the procedure that "a voltage of 3.0 V was applied between both of the electrodes to flow electricity for 10 minutes, thereby carrying out an electrochemical reaction" was not carried out. The bonding amount (J) of the cell-adhesive artificial peptide (P1-1) bonded to the cell-adhesive material for biological tissues (B1) immediately after the production was 60 ng/mm$^2$.

Comparative Example 2

Solutions were prepared by dissolving the cell-adhesive artificial peptide (P1-1) and 3-glycidoxypropyltriethoxysilane separately in deionized water each at a concentration of 200 μg/g. A material for biological tissues (titanium plate, rectangular parallelepiped having a size of 100 mm×100 mm×0.1 mm) was immersed in a solution (200 mL) prepared by mixing equal amounts of these solutions. Subsequently, the titanium plate was allowed to leave in the solution at 20 to 30° C. for 2 hours. Thereafter, the titanium plate was taken out from the solution, then subjected to a washing operation involving immersing the titanium plate in deionized water (200 mL) and immediately taking out the titanium plate therefrom three times, and then dried in an air circulation dryer at 60° C. for two hours, thereby producing a comparative cell-adhesive material for biological tissues (B2). The bonding amount (J) of the cell-adhesive artificial peptide (P1-1) bonded to the cell-adhesive material for biological tissues (B2) immediately after the production was 90 ng/mm$^2$.

Comparative Example 3

A comparative cell-adhesive material for biological tissues (B3) was produced in the same manner as in Example 1, except that the procedure that "a voltage of 3.0 V was applied between both of the electrodes to flow electricity for 10 minutes, thereby carrying out an electrochemical reaction" was not carried out and the cell-adhesive artificial peptide (P1-1) was changed to the cell-adhesive artificial peptide (P1-0). The bonding amount (J) of the cell-adhesive artificial peptide (P1-1) bonded to the cell-adhesive material for biological tissues (B3) immediately after the production was 60 ng/mm$^2$.

Comparative Example 4

A comparative cell-adhesive material for biological tissues (B4) was produced in the same manner as in Example 1, except that the cell-adhesive artificial peptide (P1-1) was changed to bovine serum albumin (BSA). The bonding amount (J) of bovine serum albumin (BSA) bonded to the cell-adhesive material for biological tissues (B4) immediately after the production was 50 ng/mm$^2$.

<Evaluation 1>
(Evaluation on Bonding Strength Between Titanium Plate and Cell-Adhesive Artificial Peptide: Bonding Amount after Ultrasonic Washing)

After applying an ultrasonic wave to a 0.5 wt % aqueous sodium dodecylsulfate (special grade reagent) solution (500 mL) in which immerse each of test specimens {cell-adhesive materials for biological tissues (A1) to (A7) and (B1) to (B4)} for 10 minutes in an ultrasonic washing device (WS-600-28S, manufactured by Tech-Jam, 28 kHz), each of the test specimens was taken out from the solution. Thereafter, a washing operation involving immersing each of the test specimens in deionized water (500 mL) and then taking out each of the test specimens from the deionized water immediately was carried out three times and each of the test specimens was dried in an air circulation dryer at 60° C. for 2 hours. The bonding amount of each of the cell-adhesive artificial peptides or bovine serum albumin (BSA) bonded to each of the test specimens was quantified by a trinitrobenzenesulfonic acid (TNBS) method in the same manner as in Example 1. The results are shown in Table 1.

<Evaluation 2>
(Evaluation by Gingival Epithelium Proliferation Test)

A gingival epithelium proliferation ratio (%) was determined in the manner mentioned below using each of test specimens {rectangular parallelepipeds prepared by cutting the cell-adhesive materials for biological tissues (A1) to (A7) and (B1) to (B4) into sizes of 6 mm×6 mm×0.1 mm}.

The gingiva was excised from the buccal gingiva of the upper jaw of a rabbit with a biopsy trepan (diameter: 6 mm) to expose the front teeth side, and then each of the test specimens (6 mm×6 mm×0.1 mm) was attached to the exposed front teeth side so that four corners of each of the test specimens were covered with the gingiva. In this manner, each of the test specimens was fixed.

Immediately after the fixation of each of the test specimens, a photograph of the surface (6 mm×6 mm) of each of the test specimens was taken from the vertical direction relative to the surface of each of the test specimens (single-lens reflex camera D70, manufactured by Nikon Corporation, magnification: 10 folds), and the surface area of the exposed part of each of the test specimens in the obtained photograph was measured (surface area G).

After 3 days, a photograph of each of the test specimens was taken in the same manner as mentioned above, the surface area of the exposed part of each of the test specimens in the obtained photograph was measured (surface area H).

The gingival epithelium proliferation rate (%) was calculated from the above-mentioned measured surface areas in accordance with the formula shown below, and the results are shown in Table 1.

Gingival epithelium proliferation rate (%)=[1−(surface area $H$/surface area $G$)]×100

<Evaluation 3>
(Evaluation on Adhesion Strength Between Titanium Plate and Buccal Gingiva of Upper Jaw of Rabbit)

Adhesion strength was determined in the manner mentioned below using each of test specimens {rectangular parallelepipeds prepared by cutting the cell-adhesive materials for biological tissues (A1) to (A7) and (B1) to (B4) into sizes of 4 mm×8 mm×0.1 mm}.

A slit having a size of about 4 mm was formed on the buccal gingiva of the upper jaw of a rabbit from the mouth side toward the throat side with a surgical knife, and each of the test specimens (4 mm×8 mm×0.1 mm) was inserted into the slit in such a manner that each of the test specimens became parallel with the front teeth.

After 8 days, the upper jaw into which each of the test specimens had been inserted was excised and then subjected to a tensile test between the gingiva and each of the test specimens using an autograph (AG-500, manufactured by SHIMADZU CORPORATION) to measure the maximum tensile strength (MPa). The results are shown in Table 1.

<Evaluation 4>
(Evaluation on Adhesion Strength Between Titanium Plate and Buccal Gingiva of Upper Jaw of Rat)

Adhesion strength was determined in the manner mentioned below using each of test specimens {cubes prepared by cutting the cell-adhesive materials for biological tissues (A1) to (A7) and (B1) to (B4) into sizes of 4 mm×0.1 mm×0.1 mm}.

The buccal gingiva of the upper jaw of a rat was removed with a surgical knife to expose teeth, and holes each having a size of 4 mm deep and 1 mm φ were formed in the exposed teeth with a drill. Each of the test specimens (4 mm×0.1 mm×0.1 mm) was inserted into the hole.

After 8 days, the upper jaw into which each of the test specimens had been inserted was excised and then subjected to a tensile test between the upper jaw and each of the test specimens using an autograph (AG-500, manufactured by SHIMADZU CORPORATION) to measure the maximum tensile strength (MPa). The results are shown in Table 1.

TABLE 1

|  |  | <Evaluation 1> Bonding amount (ng/mm²) | | <Evaluation 2> Gingival epithelium proliferation rate (%) | <Evaluations 3, 4> Maximum tensile strength (MPa) | |
|---|---|---|---|---|---|---|
|  |  | Immediately after production | After ultrasonic washing |  | Buccal gingiva of upper jaw of rabbit | Buccal gingiva of upper jaw of rat |
| Examples | 1 | 70 | 65 | 80 | 0.066 | 0.102 |
|  | 2 | 70 | 65 | 80 | 0.065 | 0.098 |
|  | 3 | 60 | 55 | 80 | 0.066 | 0.097 |
|  | 4 | 60 | 58 | 70 | 0.061 | 0.088 |
|  | 5 | 60 | 55 | 70 | 0.061 | 0.087 |
|  | 6 | 60 | 53 | 72 | 0.062 | 0.091 |
|  | 7 | 60 | 54 | 70 | 0.063 | 0.095 |
| Comparative Examples | 1 | 60 | 5 | 40 | 0.021 | 0.021 |
|  | 2 | 90 | 65 | 50 | 0.033 | 0.038 |
|  | 3 | 60 | 5 | 35 | 0.015 | 0.021 |
|  | 4 | 50 | 45 | 20 | 0.011 | 0.018 |

From the measurement results <Evaluation 1> on the bonding amounts of the cell-adhesive artificial peptides or bovine serum albumin (BSA) immediately after the production, it is found that the bonding amounts in all of Examples 1 to 7 and Comparative Examples 1 to 3 are 60 ng/mm² or more, and the bonding forces to the titanium plate in the cases where the cell-adhesive artificial peptides are used are stronger than those in the case wherein BSA is used (Comparative Example 4). Further, from the comparison between the bonding forces immediately after the production and the bonding forces after the ultrasonic washing, it is found that, in the cell-adhesive materials for biological tissues according to the present invention (Examples 1 to 7) and the comparative cell-adhesive materials for biological tissues (Comparative Examples 2 and 4), the cell-adhesive artificial peptides (or BSA) are bonded to the materials for biological tissues more strongly than the immersed/attached cell-adhesive materials for biological tissues (Comparative Examples 1 and 3).

From the results of the gingival epithelium proliferation rates <Evaluation 2>, it is found that the gingival epithelium proliferation rates in the cell-adhesive materials for biological tissues according to the present invention (Examples 1 to 7) are significantly higher than those in the comparative cell-adhesive materials for biological tissues (Comparative Examples 1 to 4), and therefore the cell-adhesive materials for biological tissues according to the present invention (Examples 1 to 7) have excellent cell proliferation properties. Further, from the results of the maximum tensile strengths <Evaluations 3, 4>, it is found that, in both the cases in which the buccal gingiva of the upper jaw of a rabbit is used and the cases in which the buccal gingiva of the upper jaw of a rat is used, the cell-adhesive materials for biological tissues according to the present invention (Examples 1 to 7) have significantly higher maximum tensile strengths than those of the comparative cell-adhesive materials for biological tissues (Comparative Examples 1 to 4), and have excellent adhesiveness between the material for biological tissues and cells.

From the above results, it is found that, in the cell-adhesive materials for biological tissues according to the present invention, the cell-adhesive artificial peptides (P) each retaining a biological activity are immobilized in large amounts in the state of keeping the biological activity, and therefore the cell-adhesive materials for biological tissues according to the present invention can be applied in medical devices having excellent adhesion to cells, cell proliferation properties and adhesion to tissues.

INDUSTRIAL APPLICABILITY

The cell-adhesive material for biological tissues according to the present invention has excellent adhesion to cells, cell proliferation properties and adhesion to biological tissues, and therefore can be used widely as medical devices such as an implant, a bone fixer, a bone cage, a dental implant, a catheter, a guide wire, a stent and an artificial joint.

SEQUENCE LISTING

The invention claimed is:

1. A cell-adhesive substrate for biological tissues, comprising:
   a cell-adhesive artificial peptide (P), and
   a substrate for biological tissues,
   wherein the cell-adhesive artificial peptide (P) is immobilized on the surface of the substrate for biological tissues through an electrochemical reaction,
   wherein the cell-adhesive artificial peptide (P) is a polypeptide (P1) which is synthesized using a genetic recombinant microorganism and has at least one cell-adhesive minimal amino acid sequence (X) in one molecule,
   wherein the cell-adhesive minimal amino acid sequence (X) is at least one sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12,
   wherein the polypeptide (P1) additionally has at least two amino acid sequences each represented by SEQ ID NO: 21 in the one molecule,
   wherein the cell-adhesive artificial peptide (P) further comprises auxiliary amino acid sequences (Y), and
   wherein the ratio of the number of the cell-adhesive minimal amino acid sequences (X) to the number of the auxiliary amino acid sequences (Y) in the cell-adhesive artificial peptide (P) is 0.002 to 10.

2. The cell-adhesive substrate for biological tissues according to claim 1, wherein the number of the cell-adhesive minimal amino acid sequences (X) in the one molecule of the polypeptide (P1) is 3 to 50.

3. A medical device comprising the cell-adhesive substrate for biological tissues according to claim 1.

4. The cell-adhesive substrate for biological tissues according to claim 1, wherein the substrate for biological tissues is a metal.

5. The cell-adhesive substrate for biological tissues according to claim 1, wherein the substrate for biological tissues is an electrically conductive ceramic.

6. The cell-adhesive substrate for biological tissues according to claim 1, wherein the substrate for biological tissues is a titanium or a titanium alloy.

7. The cell-adhesive substrate for biological tissues according to claim 1, wherein the ratio of the number of the cell-adhesive minimal amino acid sequences (X) to the number of the auxiliary amino acid sequences (Y) in the cell-adhesive artificial peptide (P) is 0.01 to 2.

8. The cell-adhesive substrate for biological tissues according to claim 1, wherein the ratio of the number of the cell-adhesive minimal amino acid sequences (X) to the number of the auxiliary amino acid sequences (Y) in the cell-adhesive artificial peptide (P) is 0.05 to 0.5.

9. The cell-adhesive substrate for biological tissues according to claim 1,
   wherein the cell-adhesive artificial peptide (P) is further modified with a compound (AM), and
   wherein the compound (AM) is a compound (AM-1) comprising a primary amino group, a secondary amino group, a tertiary amino group and/or a quaternary ammonia group, a compound (AM-2) comprising a carboxyl group, a compound (AM-3) containing a sulfo group, or a compound (AM-4) comprising a hydroxyl group.

10. The cell-adhesive substrate for biological tissues according to claim 1, wherein the number of repetitions of the amino acid sequences each represented by SEQ ID NO: 21 in the one molecule is 2 to 33.

11. The cell-adhesive substrate for biological tissues according to claim 10, wherein the number of repetitions of the amino acid sequences each represented by SEQ ID NO: 21 in the one molecule is 3 to 23.

12. The cell-adhesive substrate for biological tissues according to claim 10, wherein the number of repetitions of the amino acid sequences each represented by SEQ ID NO: 21 in the one molecule is 4 to 13.

* * * * *